(12) United States Patent
Takebayashi

(10) Patent No.: US 8,678,819 B2
(45) Date of Patent: Mar. 25, 2014

(54) SURGICAL GUIDE, AND A METHOD FOR POSITIONING A DRILL USING THE SURGICAL GUIDE

(76) Inventor: Akira Takebayashi, Saitama (JP)

( * ) Notice: Subject to any disclaimer, the term of this patent is extended or adjusted under 35 U.S.C. 154(b) by 530 days.

(21) Appl. No.: 12/992,670

(22) PCT Filed: May 18, 2009

(86) PCT No.: PCT/JP2009/059145
§ 371 (c)(1),
(2), (4) Date: Jan. 4, 2011

(87) PCT Pub. No.: WO2009/142179
PCT Pub. Date: Nov. 26, 2009

(65) Prior Publication Data
US 2011/0117516 A1   May 19, 2011

(30) Foreign Application Priority Data

May 20, 2008 (JP) .................................. 2008-131613

(51) Int. Cl.
*A61C 1/00* (2006.01)

(52) U.S. Cl.
USPC .......................................................... 433/29

(58) Field of Classification Search
USPC .............. 362/572–573, 804; 385/25–26, 147; 433/29, 72–76, 215; 434/263, 270; 606/2–3, 10–18, 96–98; 623/11.11, 623/901
See application file for complete search history.

(56) References Cited

U.S. PATENT DOCUMENTS

| 5,426,687 | A | 6/1995 | Goodall et al. |
| 5,927,973 | A * | 7/1999 | Hanebaum et al. ............. 433/72 |
| 6,254,606 | B1 * | 7/2001 | Carney et al. ................. 606/102 |
| 6,319,006 | B1 | 11/2001 | Scherer et al. |
| 6,605,092 | B2 * | 8/2003 | Grumberg et al. ............. 606/96 |
| 8,231,629 | B2 * | 7/2012 | Lerner et al. .................... 606/87 |
| 2004/0166469 | A1 * | 8/2004 | Tremont ......................... 433/68 |
| 2004/0248060 | A1 * | 12/2004 | Cozean et al. ................. 433/29 |
| 2005/0003323 | A1 * | 1/2005 | Katsuda et al. ................ 433/29 |
| 2006/0240378 | A1 * | 10/2006 | Weinstein et al. ............. 433/76 |
| 2010/0323320 | A1 | 12/2010 | Takebayashi |
| 2011/0090487 | A1 * | 4/2011 | Schmidt et al. ............ 356/152.1 |

FOREIGN PATENT DOCUMENTS

| JP | 07-51278 | 2/1995 |
| JP | 2000-312680 | 11/2000 |
| JP | 2001-170080 | 6/2001 |
| JP | 2001-212158 | 8/2001 |
| JP | 2002-85421 | 3/2002 |

* cited by examiner

*Primary Examiner* — Todd Manahan
*Assistant Examiner* — Matthew Nelson
(74) *Attorney, Agent, or Firm* — Greenblum & Bernstein, P.L.C.

(57) ABSTRACT

A surgical guide used in implant treatment. A wire is mounted to a mockup at the orientation at which an implant fixture should be embedded. A guide member of a surgical guide is fitted to a tooth portion of the mockup. The optical axis of an irradiated light beam guided by a light irradiation portion from a light emitting portion through an optical fiber is aligned with the central axis of the wire by moving and adjusting the portion supported by a wire member. Drilling is performed after the adjusted guide member is removed from the mockup and fitted to a patient's tooth portion and the central axis of a drill is aligned with the optical axis of the beam.

1 Claim, 20 Drawing Sheets

Fig. 11

On the CT display     The position and orientation of a fixture 71 to be embedded at
‖
The position and orientation a wire 31 (32)
is embedded at
= The central axis of the wire 31 (32)

On a mockup 30

The irradiating position and irradiating
orientation of the light beam L
‖ = The optical axis of the light beam L Aligned
(first positioning step)

In the mouth

The irradiating position and irradiating
orientation of the light beam L
= The optical axis of the light beam L The position and orientation of a drill 41
for forming a guide hole 42
= The central axis of the drill 41

Aligned
(second positioning step)

The tip 41a of the drill 41 is aligned with
the mark M such that the light beam L irradiates
the center of the base end portion 41b.

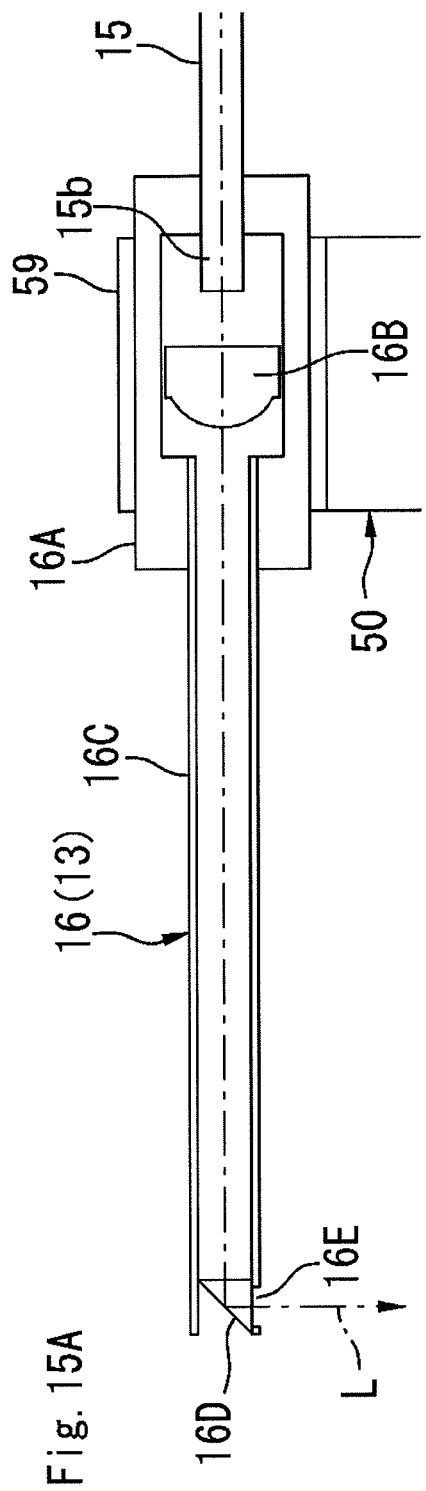

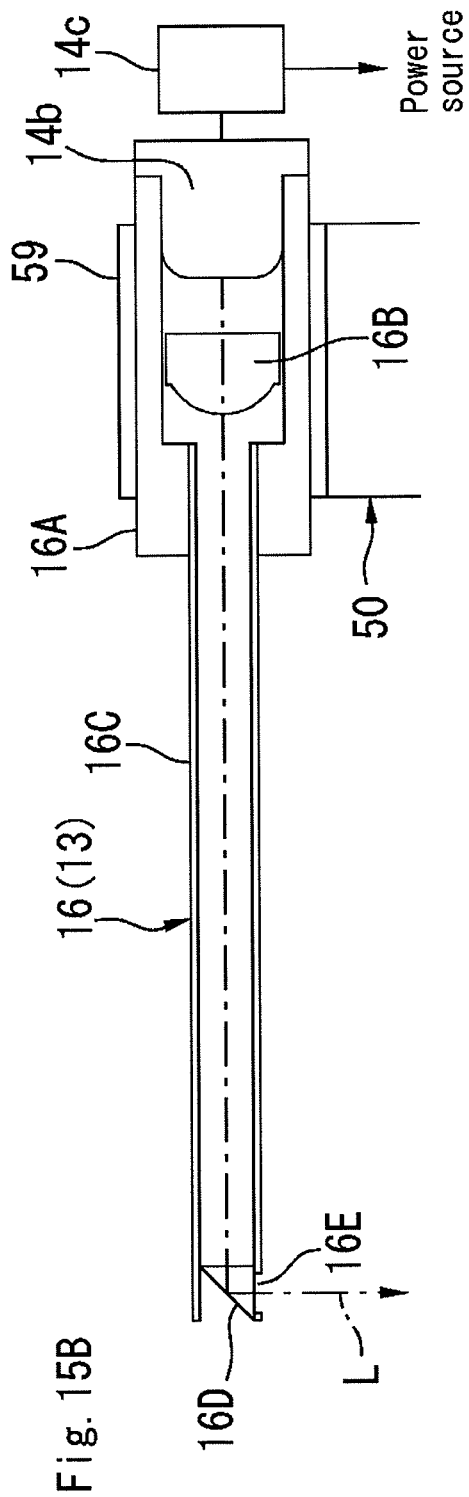

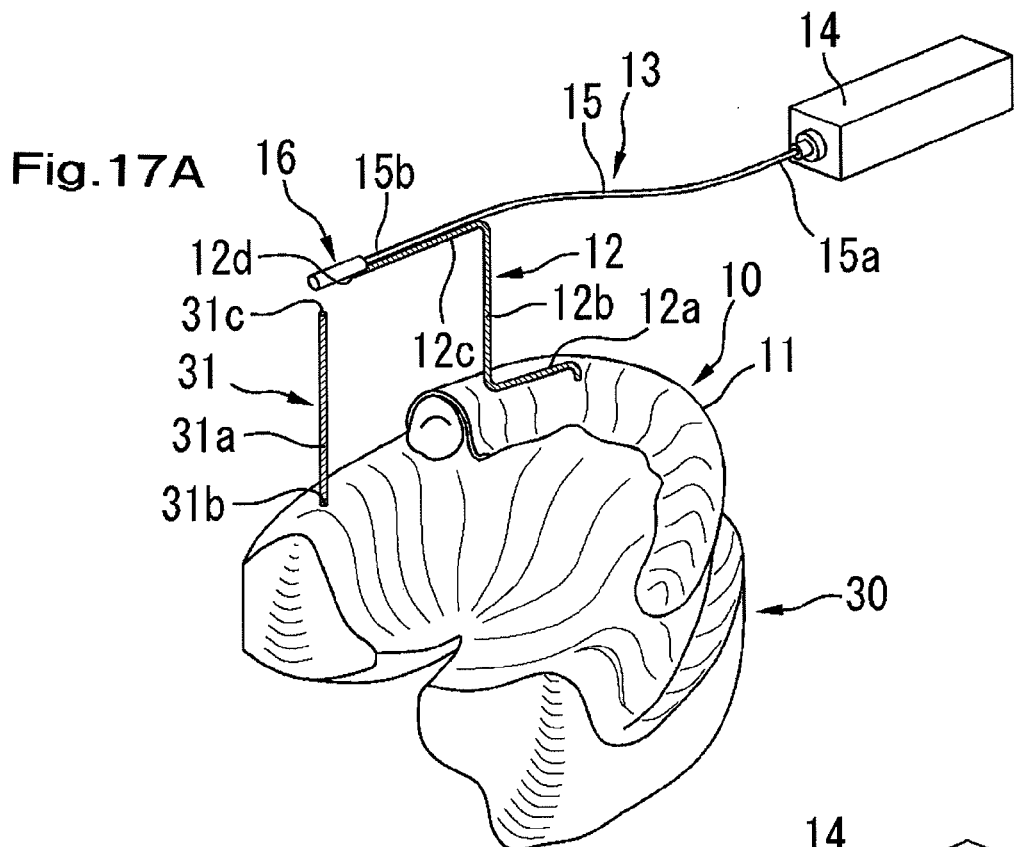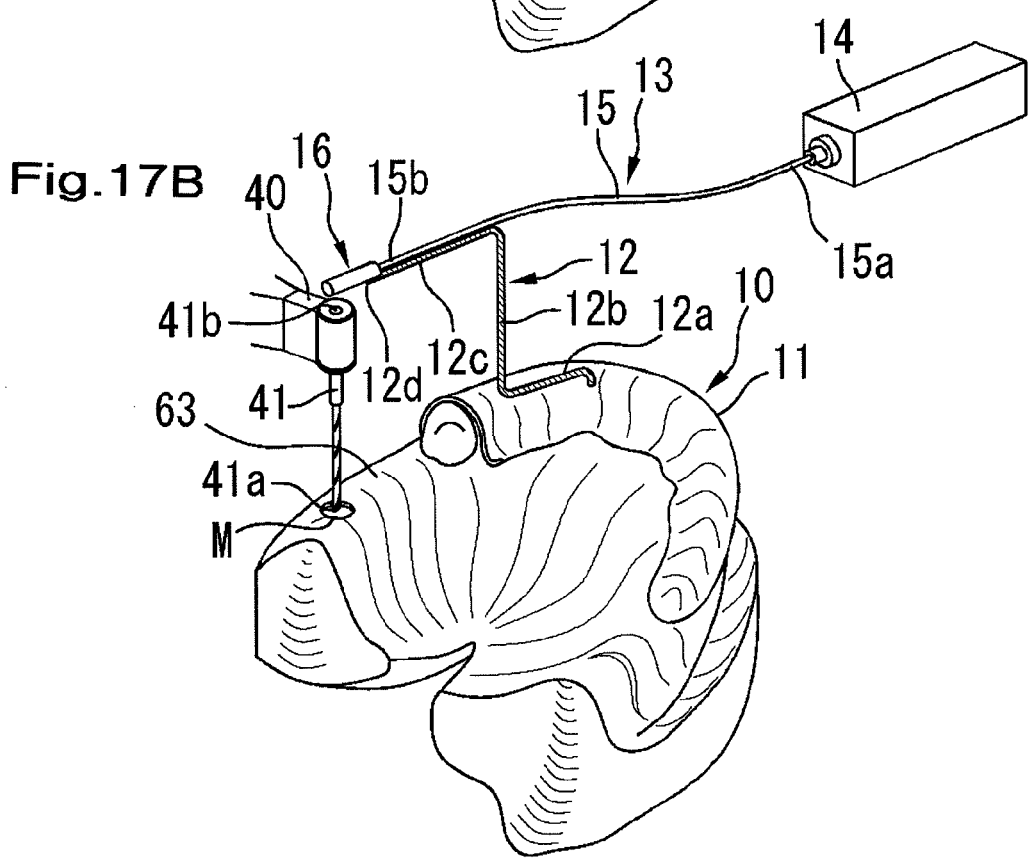

SURGICAL GUIDE, AND A METHOD FOR POSITIONING A DRILL USING THE SURGICAL GUIDE

TECHNICAL FIELD

The present invention relates to a surgical guide for positioning a drill when a guide hole into which an implant fixture is to be embedded is formed in an alveolar bone, and a method for positioning a drill using the surgical guide.

BACKGROUND

A dental implant (hereinafter simply referred to "implant") used for implant treatment is made up of a fixture (implant body, for example, made of titanium) to be embedded into an alveolar bone at which a tooth is missing, an abutment coupled to and supporting the fixture, and a superstructure (artificial tooth crown) attached to the abutment. In the implant treatment that uses this type of implant, it is very important to accurately forming a guide hole, into which the fixture is to be embedded, in the alveolar bone (see JP-A-2001-170080, for example).

Implant treatment can be categorized into two types: prosthetically oriented treatment (top-down treatment) and exist-bone orientated treatment. In the former, prosthetically oriented treatment, a mockup (full-scale plaster model) of teeth and alveolar ridges of a patient is created. The mockup is mounted to an articulator in order to determine the geometries and position of a functionally and aesthetically ideal prosthesis (superstructure). Based on the determination, the position at which the fixture is to be embedded is decided. In the latter, exist-bone orientated treatment, the position that is surgically and anatomically ideal for the fixture to be embedded at is determined based on the condition of the alveolar bone (the width, thickness, and density of the alveolar bone, the course of the nerve, or other factors) of a patient.

Currently, simulation software in which CT (computed tomography apparatus) or other apparatus is utilized may be used for determining the position that is prosthetically (functionally and aesthetically) ideal for the fixture to be embedded at, in consideration of the condition of the alveolar bone or other factors of the patient. In addition, a stent that contains a contrast medium may be used in CT scanning in order to display onto the mockup the position that is determined on a CT display as a position the fixture is to be embedded at.

When a guide hole into which a fixture is to be embedded is drilled in an alveolar bone of a patient, three-dimensional positioning of the drill in the mouth of the patient is required. However, it is quite difficult to accurately form a guide hole by freehand at the position the fixture should be embedded while looking at the CT display or the mockup. Therefore, various jigs, i.e., surgical guides, have been devised.

A typical example is a surgical guide that has a metallic guide ring for guiding a drill to the position at which the fixture should be embedded. When a drill is placed into a hole in the guide ring and inserted along the hole in the guide ring, the drill is guided such that a guide hole is formed at the position the fixture should be embedded.

SUMMARY

However, the surgical guides having a guide ring as described above have problems as follows.

(1) The surgical guide covers the surgical site, and a dentist cannot visually identify the portion of the alveolar bone the tip of the drill is cutting, and thus the dentist may feel uneasy.

(2) A slight gap (free space) is required between the drill and the hole in the guide ring. However, the gap (free space) may allow the drill to tilt more than necessary because the thickness of the guide ring is thinner than the length of the drill. As a result, a hole having an inaccurate orientation may be formed.

(3) The alveolar bone in which the hole is to be formed is covered with the guide ring and periphery portions thereof, and the hole in the guide ring is blocked by the drill. As a result, a closed space is formed around the alveolar bone. Therefore, it is difficult to provide sufficient cooling water to the alveolar bone to be cut, which may cause bone burns.

(4) Various types of drills are used to form the guide hole into which the fixture is to be embedded. At first, a pilot drill having a small diameter is used, and then drills, each having a slightly larger diameter than the diameter of the drill used in the preceding drilling, are used. As a result, several types of surgical guides, each of which corresponds to each drill, are required, which increases cost.

Therefore, an aim of the present invention is to provide a surgical guide which enables a dentist to visually identify the tip of the drill, and which will not allow the drill to tilt more than necessary, and which enables sufficient cooling water to be provided and thus will not easily cause bone burns, and which is compatible with several types of drills having different diameters; and a method for positioning the drill using the surgical guide.

Means to Solve the Problems

The invention according to claim 1 relates to a surgical guide used for reproducing in the mouth of a patient the position and orientation of a wire that is embedded in a mockup that imitates inside of the mouth of the patient with the intention of indicating the position and orientation of a drill when a guide hole, into which a dental implant fixture is to be embedded in the mouth of the patient, is formed.

The surgical guide according to the invention is characterized in that the surgical guide includes:

(1) a detachably attachable guide member to be fitted to a tooth portion of the mockup, and to a tooth portion of the patient that corresponds to the tooth portion of the mockup, (2) a light irradiation apparatus that includes a light emitting portion for emitting light, and a light irradiation portion for irradiating the light emitted at the light emitting portion as a spot-beam like light beam toward a tip of the wire, and (3) a supporting member, the base end portion thereof being mounted to the guide member, and the tip portion of the supporting member being capable of supporting at least the light irradiation portion of the light irradiation apparatus such that the irradiating position and irradiating angle of the light beam that is irradiated from the light irradiation portion toward the tip of the wire can be adjusted.

The invention according to claim 2 is characterized in that the light irradiation apparatus in the surgical guide of claim 1 includes a laser module as the light emitting portion, and an optical fiber for guiding the light emitted at the laser module, and the light irradiation portion is configured by bending a tip of the optical fiber.

The invention according to claim 3 is characterized in that the light irradiation apparatus in the surgical guide of claim 1 includes a laser module as the light emitting portion, and an optical fiber for guiding the light emitted at the laser module, and the light irradiation portion is configured by providing an inclined surface at a tip of the optical fiber, and the inclined surface serves as a total reflection surface.

The invention according to claim 4 is characterized in that the light irradiation apparatus in the surgical guide of claim 1 includes a laser module as the light emitting portion, an optical fiber for guiding the light emitted at the laser module, and a prism provided at a tip of the optical fiber and configuring the light irradiation portion.

The invention according to claim 5 is characterized in that the light irradiation apparatus in the surgical guide of claim 1 includes a laser pointer mounted to an intermediate portion of the supporting member and serving as the light emitting portion, and a prism for configuring the light irradiation portion that irradiates the light emitted at the laser pointer toward the tip of the wire.

The invention according to claim 6 is characterized in that the laser pointer in the surgical guide of claim 5 is mounted adjacently to the prism.

The invention according to claim 7 is characterized in that the surgical guide of claim 1 includes a laser diode as a light irradiation apparatus being supported at a tip end portion of the supporting member, and the light irradiation apparatus emits light and irradiates the emitted light toward the tip of the wire.

The invention according to claim 8 is characterized in that the supporting member in the surgical guide of claim 1 is configured by a plastically deformable wire member.

The invention according to claim 9 is characterized in that the light irradiation apparatus in the surgical guide of claim 1 includes a laser module as the light emitting portion, and an optical fiber for guiding the light emitted at the laser module, and the light irradiation portion is configured by a hollow pipe for surrounding the optical fiber and a lens and a prism that are provided at a tip of the optical fiber and mounted to a tip of the hollow pipe.

The invention according to claim 10 is characterized in that the light irradiation apparatus in the surgical guide of claim 1 includes a laser module as the light emitting portion, and an optical fiber for guiding the light emitted at the laser module, and the light irradiation portion is configured by a lens and a hollow pipe that are provided at a tip of the optical fiber, and a prism mounted to a tip of the hollow pipe.

The invention according to claim 11 is characterized in that the supporting member in the surgical guide of claim 1 is configured by a jig being capable of moving and adjusting at least the light irradiation portion of the light irradiation apparatus to a given position and at a given angle.

The invention according to claim 12 relates to a method for positioning a drill using a surgical guide for reproducing in the mouth of a patient the position and orientation of the drill with respect to the wire embedded in a mockup that imitates inside of the mouth of the patient with the intention of indicating the position and orientation of the drill when a guide hole, into which a dental implant fixture is embedded, is formed.

The method for positioning the drill according to the invention is characterized in that the method uses a surgical guide that includes:

(1) a detachably attachable guide member to be fitted to a tooth portion of the mockup and to a tooth portion of the patient that corresponds to the tooth portion of the mockup, (2) a light irradiation apparatus that includes a light emitting portion for emitting light, and a light irradiation portion for irradiating the light emitted at the light emitting portion as a spot-beam like light beam toward a tip of the wire, and (3) a supporting member, the base end portion thereof being mounted to the guide member, and the tip end portion of the supporting member being capable of supporting at least the light irradiation portion of the light irradiation apparatus such that the irradiating position and irradiating angle of the light beam that is irradiated from the light irradiation portion toward the tip of the wire can be adjusted, and the method includes:

(4) a first positioning step in which the guide member is fitted to the tooth portion of the mockup, and the light irradiation portion supported by the supporting member is moved and adjusted such that the spot-beam like light beam is aligned with the central axis of the wire, and (5) a second positioning step in which the guide member is removed from the tooth portion of the mockup and fitted to the tooth portion of the patient such that the central axis of the drill is aligned with the spot-beam like light beam.

Effect of The Invention

According to the present invention, the guide member of the surgical guide is fitted to the tooth portion of the mockup, and the position and angle of the light irradiation portion is moved and adjusted by the supporting member as appropriate such that the optical axis of the light beam that is irradiated from the light irradiation portion is aligned with the central axis of the wire. After that, the guide member of the surgical guide is removed from the tooth portion of the mockup and fitted to the tooth portion of the patient, and drilling is performed in a condition in which the central axis of the drill is aligned with the optical axis of the light beam that is irradiated from the light irradiation portion. By these operations, a guide hole can be accurately formed in the mouth at the position and orientation same as those of the wire on the mockup. Furthermore, a dentist can see the surgical site, and can cut the alveolar bone while visually identifying the tip portion of the drill. In addition, the dentist can cut the alveolar bone while visually confirming that the drill does not tilt more than necessary; in other words, the axis of the drill does not deviate from the optical axis of the light beam. Moreover, cooling water can be sufficiently provided, which is less likely to cause bone burns. In addition, a same surgical guide can be used for drills having different diameters. The present invention has advantages as described above.

BRIEF DESCRIPTION OF THE DRAWINGS

FIG. 1 to FIG. 6, and FIGS. 17A and 17B illustrate a first embodiment. FIG. 1 is a perspective view in which a surgical guide 10 is fitted to a mockup (plaster model) 30.

FIG. 2 is a schematic view illustrating the positioning of a drill 41.

FIG. 3 is an enlarged vertical cross sectional view of a light irradiation portion 16.

FIG. 5 is a schematic view illustrating a first modification of the light irradiation portion 16 in the first embodiment.

FIG. 6 is a schematic view illustrating a second modification of the light irradiation portion 16 in the first embodiment.

FIG. 11 illustrates a principle in which the position and orientation of a wire 31 embedded in the mockup 30 are reproduced in the mouth as the position and orientation of the drill 41 (the position and orientation of a fixture 71 to be embedded at).

FIG. 12A is a perspective view illustrating the surgical guide 10 mounted to the mockup (plaster model) 30, and FIG. 12B is a perspective view illustrating the surgical guide 10 mounted in the mouth of a patient.

FIG. 14A is a perspective view illustrating the surgical guide 10 mounted to the mockup (plaster model) 30, and FIG. 14B illustrates the surgical guide 10 mounted in the mouth of the patient.

FIG. 15A is a schematic view (cross sectional view) illustrating the light irradiation portion 16 of the light irradiation apparatus 13 in the fifth embodiment. FIG. 15B illustrates a modification of the light irradiation portion 16.

FIG. 16A is a top view, FIG. 16B is a side view, and FIG. 16C is a front view.

FIGS. 17A and 17B illustrate a positioning method of the first embodiment. FIG. 17A illustrates a first positioning step, and FIG. 17B illustrates a second positioning step.

DETAILED DESCRIPTION OF THE PREFERRED EMBODIMENTS

Figure 1:
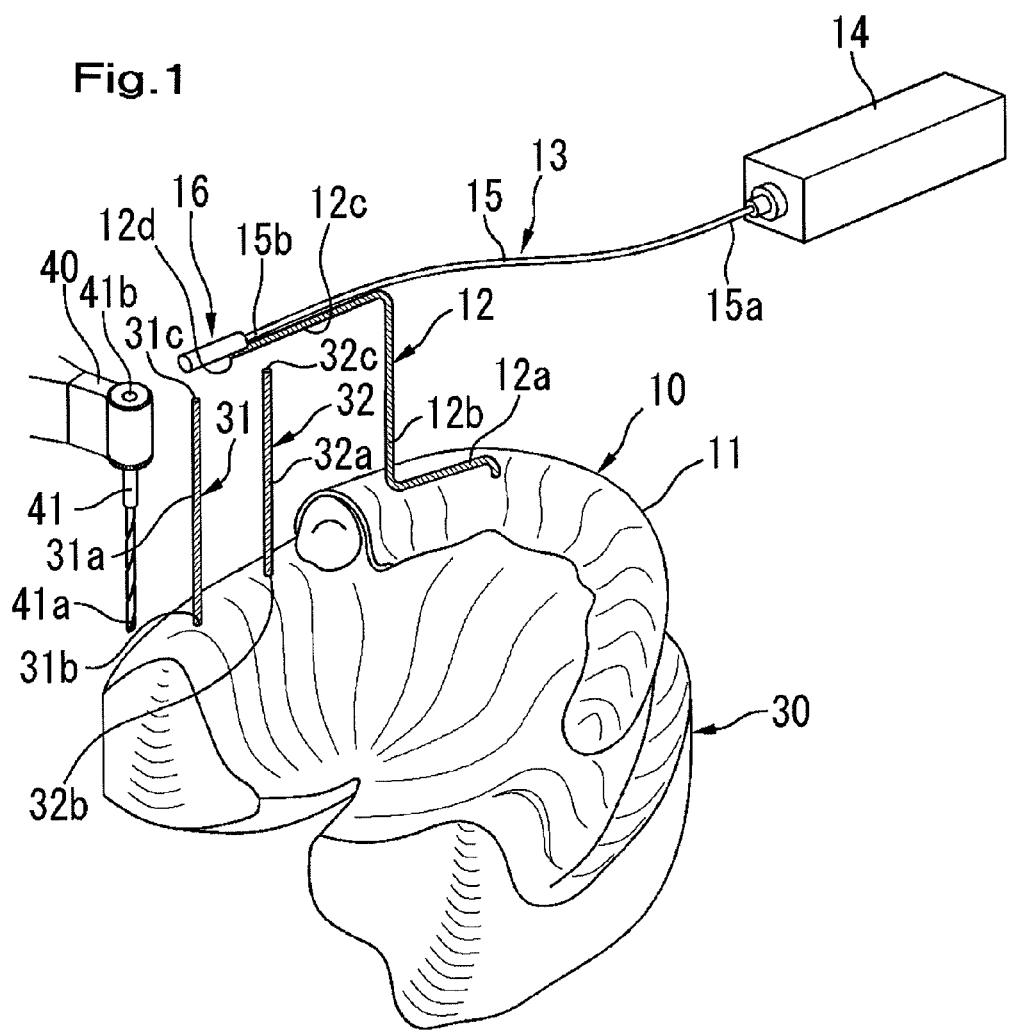

Preferred embodiments of the present invention are described in detail with reference to the drawings. Same references are used throughout the drawings to designate like or equivalent configuration, and duplicated description thereof is omitted as appropriate. In addition, components that are not essential for explanation are omitted in the drawings as appropriate.
Embodiment 1

Figure 2:
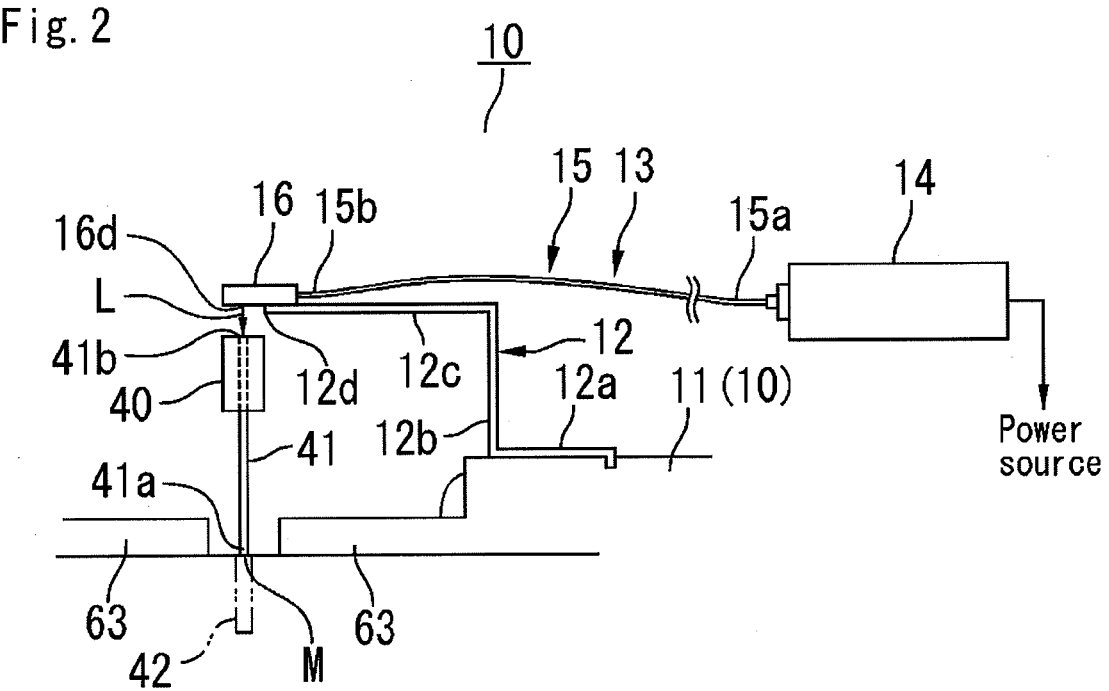
Figure 3:
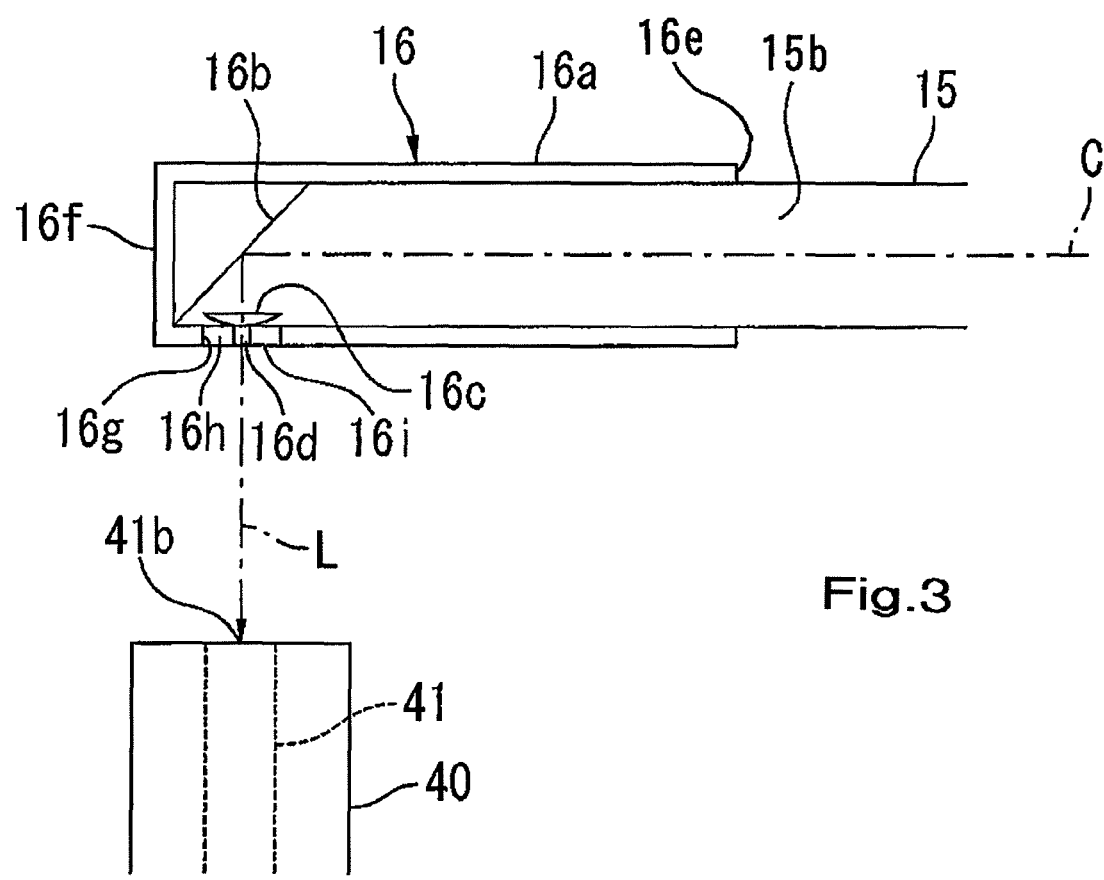
Figure 4A:
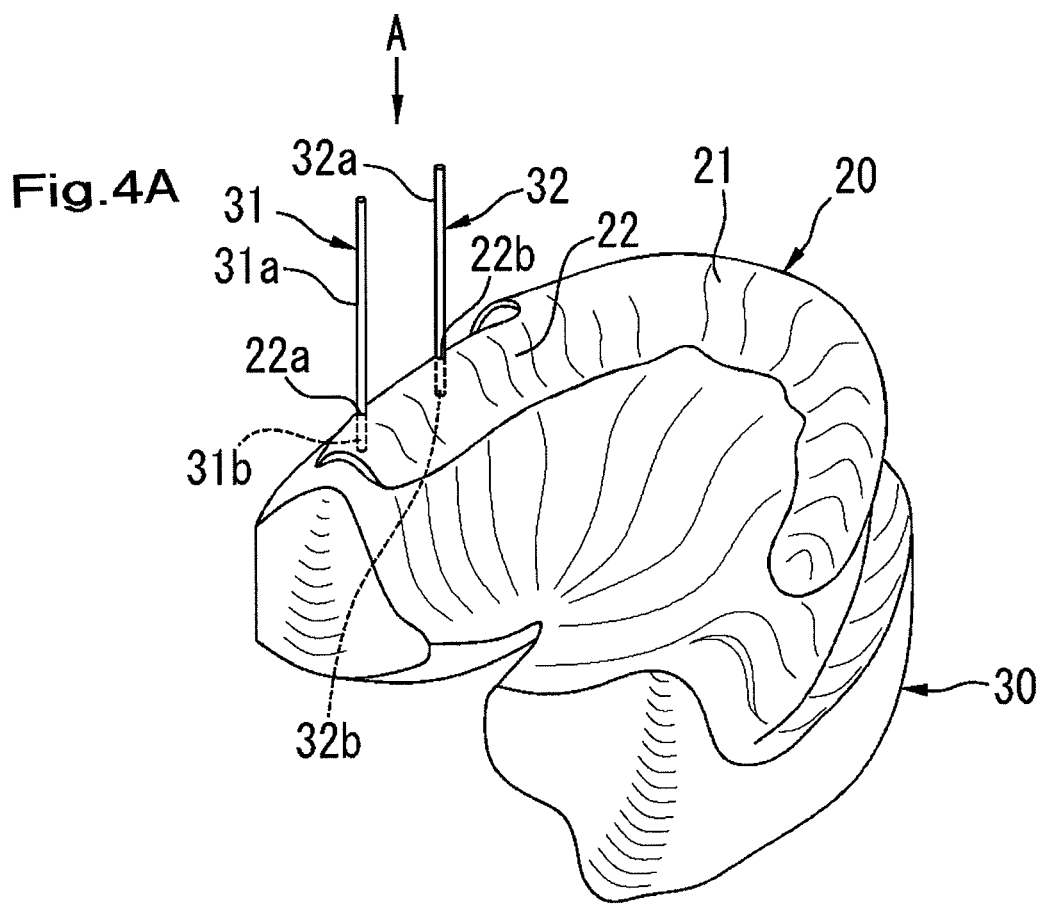
FIG. 4A is a perspective view in which another surgical guide 20 is fitted to the mockup 30.
Figure 4B:
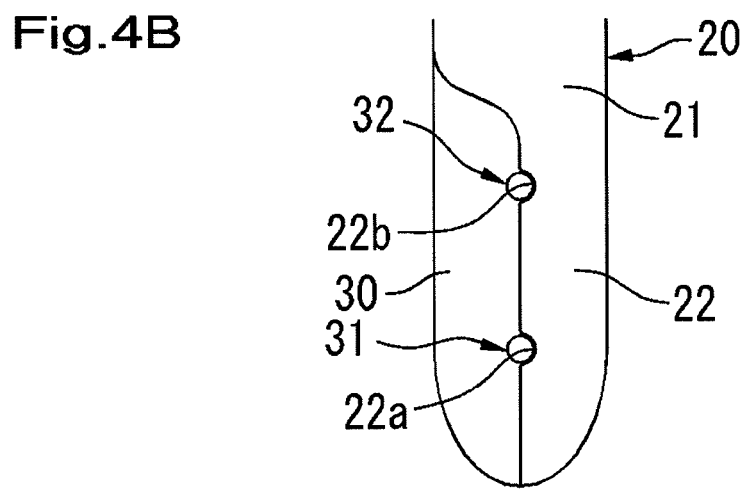
FIG. 4B is a view as seen from a direction of the arrow A in FIG. 4A.
Figure 5:
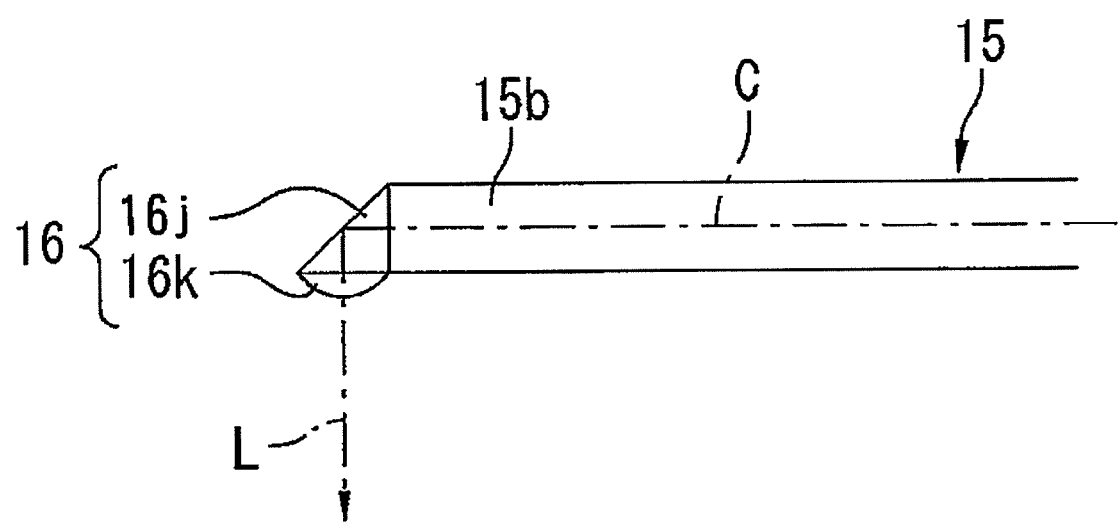
Figure 6:
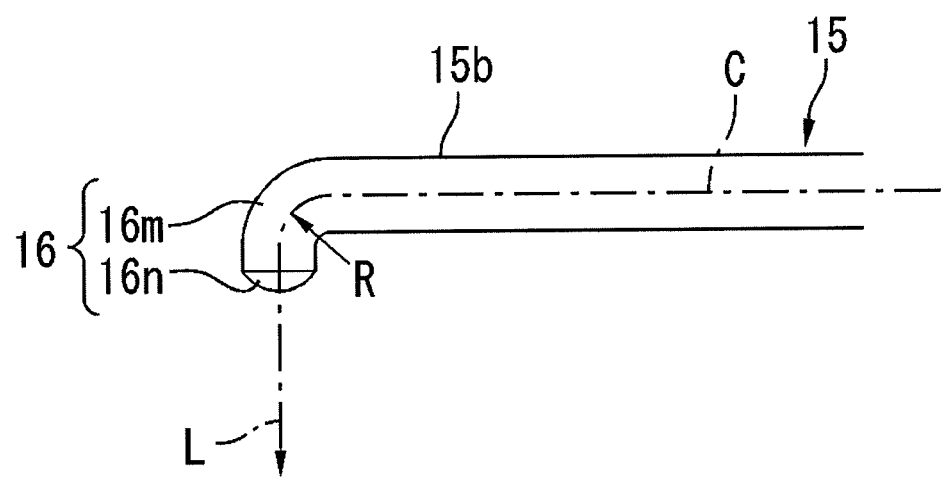
Figure 10:
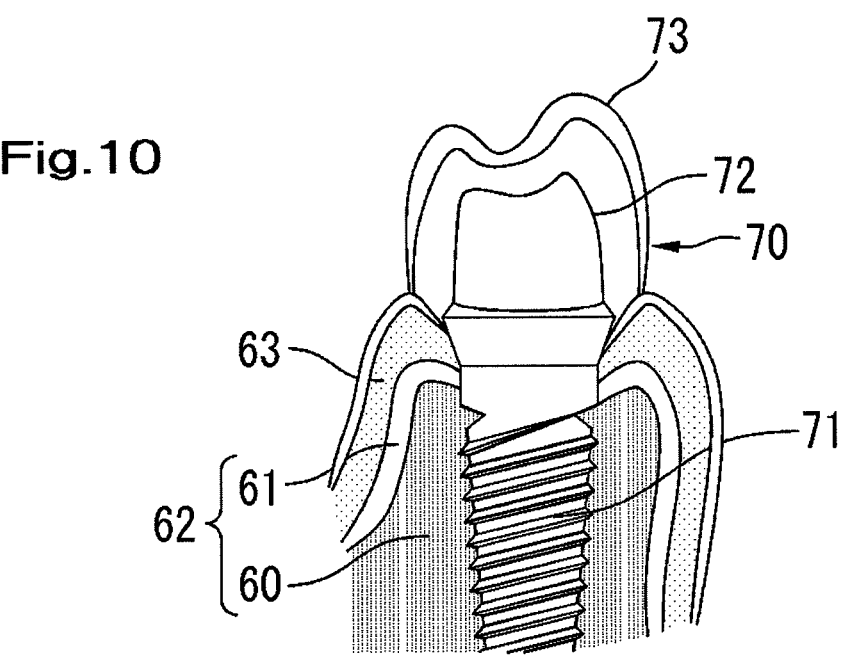
FIG. 10 is a vertical cross sectional view illustrating an implant 70.

A surgical guide 10 and a method for positioning a drill 41 according to a first embodiment are described with reference to FIG. 1 to FIG. 6, FIG. 10, FIG. 11, and FIGS. 17A and 17B. FIG. 1 is a perspective view illustrating the surgical guide 10 fitted to a mockup (plaster model) 30. FIG. 2 is a schematic view illustrating the positioning of a drill 41. FIG. 3 is an enlarged vertical cross sectional view of a light irradiation portion 16. FIG. 4A is a perspective view in which another surgical guide 20 is fitted to the mockup 30. FIG. 4B is a view as seen from a direction of the arrow A in FIG. 4A. FIG. 5 is a schematic view illustrating a first modification of the light irradiation portion 16 in the first embodiment. FIG. 6 is a schematic view illustrating a second modification of the light irradiation portion 16 in the first embodiment. FIG. 10 is a vertical cross sectional view illustrating an implant 70. FIG. 11 illustrates the principle in which the position and orientation of a wire 31 embedded in the mockup 30 are reproduced in the mouth as the position and orientation the drill 41 (the position and orientation of a fixture 71 to be embedded at). FIG. 17A illustrates a first positioning step, and FIG. 17B illustrates a second positioning step. The description hereinafter illustrates an example in which implant treatment is performed at a position where two upper right back teeth (molar teeth) of a patient are missing.

The implant 70 is described with reference to FIG. 10. A bone 62 composed of a soft cancellous bone 60 and a hard cortex bone 61, and a mucosa 63 that covers the bone 62 remain at the portion the teeth (not shown) are missing. The implant 70 includes a fixture 71 embedded into an embedding hole (guide hole) 42 formed in the bone 62, an abutment 72 coupled to the fixture 71 and serving as a support, and a superstructure 73 attached to the abutment 72.

The mockup 30 shown in FIG. 1 is a full-scale model for the upper jaw made by molding (impression of) the inside of the mouth of the patient, and made of plaster. FIG. 1 illustrates an example in which two upper right back teeth are missing. Wires 31 and 32 are embedded linearly at positions each corresponding to the center of each of the back teeth (molar teeth) in the portion the back teeth are missing. Each of these wires 31 and 32 indicates the position and orientation the fixture 71 is to be embedded at when implant treatment is performed. In the example shown in FIG. 1, the length of protruding portions 31a and 32a of the wires 31 and 32 each protruding from the mockup 30, in other words, the length from each of base end portions 31b and 32b thereof to each of tip portions 31c and 32c, is set to a length obtained by subtracting the thickness of the mucosa 63 at that portion measured on a CT display from the length of the drill (pilot drill) 41 that is used for forming an embedding hole and mounted to a contra head 40 shown in FIG. 1. The position of the wires 31 and 32 described above may be determined as described hereinafter, for example. The relative positioning between the position and orientation of the fixture 71 (see FIG. 10) to be embedded at that are determined by CT-based simulation software and the position of a CT scanning template (stent) that contains a contrast medium is measured on the CT display. Based on the measured value, a mark that indicates the orientation of the fixture 71 to be embedded at is putted to the CT scanning template (stent) that contains the contrast medium. The marked template is mounted to the mockup 30, and two holes each having a diameter of about 1 mm and a depth of about 10 mm are formed in the mockup 30 using the mark as a guide. The wires 31 and 32 are embedded into these holes respectively. By these operations, the orientation of the fixture 71 to be embedded at based on the simulation can be displayed on the mockup 30 as the orientation the wires 31 and 32 are embedded at. In other words, a drilling operation may be performed by the drill 41 mounted to the contra head 40 at the orientation same as the orientation of these wires 31 and 32, in the mouth of the patient.

The surgical guide 10 shown in FIG. 1 includes a guide member 11, a wire member (supporting member) 12 mounted to the guide member 11, and a light irradiation apparatus 13.

The guide member 11 is formed of a resin material (for example, self-curing resin) such that it conforms to the remaining dentition of the patient. The guide member 11 is detachably attachable to a tooth portion of the mockup 30 that corresponds to the remaining dentition of the patient. The position of the wire member 12 described later with respect to the tooth portion of the mockup 30 can be determined when the guide member 11 is attached and fitted to the mockup 30. The guide member 11 is detachably attachable also to the remaining dentition of the patient. The position of the wire member 12 with respect to the remaining dentition can be determined when the guide member 11 is attached and fitted to the remaining dentition.

The wire member 12 shown in FIG. 1 is formed of a wire similar to those of the wires 31 and 32 described above, and is plastically deformable. The wire member 12 is cranked, and a base end side (base end portion) 12a thereof is mounted (fixed) to the guide member 11, and an intermediate portion 12b thereof stands substantially perpendicularly, and a tip end side (tip end portion) 12c thereof extends substantially laterally toward the wires 31 and 32, and a tip end 12d is located above the tip portion 31c of the wire 31.

The light irradiation apparatus 13 includes a laser light source (laser module) 14 as a light emitting portion, an optical fiber 15 whose base end portion 15a being coupled to the laser light source 14, and a light irradiation portion 16 provided at a tip portion 15b of the optical fiber 15.

The laser light source (laser module) 14 may be made of, for example, a semiconductor laser (laser diode) and an APC (automatic power controller), and may emit a laser light beam L, for example, having a wavelength of about 532 nm to 670 nm toward the base end portion 15a of the optical fiber 15.

The optical fiber 15 may be a general fiber having a diameter of about 1 mm, and may guide the light L emitted from the laser light source 14 described above to the light irradiation portion 16.

FIG. 3 is an enlarged vertical cross sectional view of the light irradiation portion 16. The light irradiation portion 16 includes a cap 16a covering the tip portion 15b of the optical fiber 15, an inclined surface 16b formed at a tip of the optical fiber 15, a collimate-treated portion (or collimator lens) 16c disposed below the inclined surface 16b, and a dot aperture 16d provided below the collimate-treated portion (or collimator lens) 16c, as shown in FIG. 3. The cap 16a may have the inner diameter of about 1 mm, for example. An opening 16e into which the tip portion 15b of the optical fiber 15 is inserted is formed at the base end portion of the cap 16a (on the right side in FIG. 3). The tip portion of the cap 16a is closed by a lid 16f. The inclined surface 16b, which configures a total reflection surface, is formed by cutting the tip end of the optical fiber 15 at 45 degrees with respect to a level surface, and by mirror-finishing the tip end. The laser light beam L (see the optical axis C), guided to the tip portion 15b from the base end portion 15a through the optical fiber 15, is totally reflected by the inclined surface 16b, at which the orientation of the laser light beam L is changed substantially downward. The collimate-treated portion (or collimator lens) 16c is used for changing the totally reflected laser light beam L into a cylindrical (beam-like) shape. The dot aperture 16d is used for limiting the diameter of the laser light beam L. The dot aperture 16d is a through hole having a diameter of about 0.1 mm through which the laser light beam L passes, and is formed by depositing a metal on a surface 16i of a substantially circular glass plate 16h that is fitted into a circular window portion 16g formed in the cap 16a, and by leaving a non-deposited portion having a diameter of 0.1 mm at the center in a radial orientation of the glass plate 16h. The light irradiation portion 16 is mounted (fixed) to the tip end side 12c of the wire member 12 such that the dot aperture 16d slightly protrudes from the tip end 12d of the wire member 12, as shown in FIG. 2. The portion of the optical fiber 15 except the light irradiation portion 16, for example, the portion disposed along the tip end side 12c of the wire member 12 in FIG. 2, may be roughly fixed to the tip end side 12c if it otherwise adversely affects the handling of the surgical guide 10. The laser light beam L is collimated (changed into a cylindrical shape) when it passes through the collimate-treated portion (or collimator lens) 16c. The diameter of the laser light beam L is limited and the light beam becomes a spot-beam like light beam L when the light passes though the dot aperture 16d. The wire member (supporting member) 12 described above is plastically deformable, and thus the wire member (supporting member) 12 can be deformed and moved to a given position and released at the moved position in order to retain the position of the entire light irradiation portion 16.

Instead of the collimate-treated portion (or collimator lens) 16c and the dot aperture 16d described above, a dot aperture that is formed by depositing a metal directly on a surface of a collimator lens may be used.

The positioning of the drill 41 in the mouth is performed by using the surgical guide 10 having a configuration as described above.

At first, the guide member 11 of the surgical guide 10 shown in FIG. 1 is mounted and fitted to the tooth portion of the mockup 30. At this moment, the light irradiation portion 16 supported by the wire member 12 is located substantially above the tip portion 31c of the wire 31 embedded in the mockup 30.

The laser light source (light emitting portion) 14 is switched on so that the laser light beam L emitted from the laser light source (light emitting portion) 14 is guided through the optical fiber 15 to the light irradiation portion 16. The orientation of the laser light beam L is changed at approximately 90 degrees at the light irradiation portion 16, and the laser light beam L is irradiated toward the tip portion 31c of the wire 31 located below.

After that, the light irradiation portion 16 is positioned by moving the light irradiation portion 16 in order to make fine adjustments of the irradiating position and irradiating angle of the light beam L that is irradiated from the light irradiation portion 16 such that the light beam L is aligned with the central axis of the wire 31 (first positioning step) (see FIG. 17A).

The guide member 11 is removed from the mockup 30 with the first positioning being maintained, and mounted and fitted to the tooth portion of the patient. At this moment, the irradiating position and irradiating angle of the light beam L that is irradiated from the light irradiation portion 16 become the position and orientation the fixture 71 is to be embedded at, in other words, the position and orientation of the drill 41 when the embedding hole (guide hole) 42 is formed. The portion irradiated by the light beam L, on a mucosa surface of the patient, is marked using an electrosurgical knife (not shown) or other device. The mucosa 63 at the marked portion is removed by punching or flapping, and a mark (entrance point) M is put on the bone surface by using a marking bar (not shown). By these operations, the position of the tip 41a of the drill 41 when the hole (guide hole) 42, into which the fixture 71 is to be embedded, is formed by the drill 41 can be determined.

The drill 41 is mounted to the contra head 40 and drilling is performed by the drill 41. At this moment, the tip 41a of the drill 41 is aligned with the mark M, and the center of the base end portion 41b of the drill 41 is aligned so that the center is irradiated by the light beam L from the light irradiation portion 16. By these operations, the center of rotation of the drill 41 can be aligned with the light beam L, in other words, aligned with the central axis of wire 31 (second positioning step) (see FIG. 17B). The embedding hole (guide hole) 42 can be formed with high accuracy at a given position and a given orientation when drilling is performed with the second positioning being maintained, in other words, the position of the drill 41 is maintained such that the center of the base end portion 41b of the drill 41 is irradiated by the light beam L. FIG. 11 illustrates the principle of a series of these operations.

After that, another embedding hole (guide hole) 42 that correspond to another wire 32 may be formed. The embedding hole (guide holes) 42 can be formed with high accuracy by repeating operations that are similar to those of the series of operations used for forming the embedding hole (guide hole) 42 that corresponds to the wire 31 described above.

According to the first embodiment, the tip of the drill 41 can be visually identified using the surgical guide 10 that has a simple configuration, and the surgical guide 10 will not allow the drill 41 to tilt more than necessary, and the surgical guide 10 enables sufficient cooling water to be provided and thus will not easily cause bone burns, and the surgical guide 10 can be compatible with several types of drills 41 having different diameters.

In addition, according to the first embodiment, the portion of the light irradiation portion 16, which emits the light beam L, becomes a closed space covered with the cap 16a and the glass plate 16h. Therefore, the reduction in the light amount of the light beam L, for example, due to the adhesion of dust or blood to the collimate-treated portion (or collimator lens) 16c can be prevented. Furthermore, cooling water used when drilling is performed or a chemical solution used for disinfection can be prevented from seeping into the light irradiation portion 16.

According to the first embodiment, the light irradiation apparatus 13 is configured by the light irradiation portion 16, which can be made relatively compact, and the light emitting portion 14, which tends to become relatively large (as compared with the light irradiation portion 16), and these portions are coupled with the optical fiber 15. By adopting such a configuration, the light irradiation portion 16 that is inserted in the mouth of the patient together with the guide member 11 and the wire member 12 can be made compact. This may reduce the burden of the patient, who otherwise needs to widely open the mouth during the treatment. Therefore, the first embodiment is suitable not only for an implant 70 that is provided to a foretooth portion or a premolar tooth portion, but also for an implant 70 that is provided to a molar teeth portion.

In the description above, the mark M is put at the portion irradiated by the light beam L from the light irradiation portion 16. However, alternatively, the mark M may be put by using the surgical guide 20 as shown in FIGS. 4A and 4B as a jig. More specifically, the surgical guide 20 is configured by a guide member 21 and a wire guide 22 by using a resin (for example, self-curing resin) material, and formed integrally to conform to the remaining dentition of the patient and the wires 31 and 32, as shown in FIGS. 4A and 4B. The wire guide 22 is formed such that left half in the direction of the width of the guide member 21 (in a lateral direction in FIG. 4B) is cut out as shown in FIG. 4B. The portions that correspond to the wires 31 and 32 form half circular base end guides 22a and 22b. The guide member 21 is mounted and fitted to the tooth portion of the patient, and the portions on the mucosa surface that correspond to the base end guides 22a and 22b are marked by using an electrosurgical knife (not shown) or other device. The mucosa 63 at the marked portions is removed by punching or flapping. After that, a mark (entrance point) M is put on the bone surface by using a marking bar (not shown). By these operations, the position of the tip 41a of the drill 41 when the hole (guide hole) 42, into which the fixture 71 is to be embedded, is formed by the drill 41 can be determined. The positioning of the base end portion 41b of the drill 41 is made such that the light beam L from the light irradiation portion 16 impinges on the center of the base end portion 41b, similarly to the description above.

FIG. 5 illustrates a first modification of the first embodiment. In the first modification shown in FIG. 5, the light irradiation portion 16 is configured by a prism 16j and a collimator lens 16k. Other configuration is same as the configuration described above. The tip portion 15b of the optical fiber 15 is cut perpendicularly with respect to the optical axis C, as shown in FIG. 5. The prism 16j is attached to the cut portion, and the collimator lens 16k is disposed on the lower surface of the prism 16j. With this configuration, the laser light beam L guided by the optical fiber 15 is irradiated toward the wire 31 (see FIG. 1) located below. In this modification, the light irradiation portion 16 may be configured, for example, by welding the prism 16j to an end surface of the optical fiber 15 having a diameter of about 2 mm, and welding the collimator lens 16k to the lower surface of the prism 16j. The light irradiation portion 16 is fixed to the tip end side 12c of the wire member 12. In this modification, the prism 16j and the collimator lens 16k may be disposed reversely. In that case, the end surface of the optical fiber 15 may be collimate-treated, instead of using the collimator lens 16k.

FIG. 6 illustrates a second modification of the first embodiment. In the second modification, the laser light beam L guided by the optical fiber 15 is irradiated toward the wire 31 by providing a bent portion 16m at the tip portion 15b of the optical fiber 15. If the radius of curvature R of the bent portion 16m is too small, the optical fiber 15 may be broken. Therefore, in a case where the diameter of the optical fiber 15 is about 1 mm, for example, the bent portion 16m may be formed such that the radius of curvature R becomes equal to or greater than 2.5 mm. A collimator-lens treatment 16n having the shape of a collimator lens is made at the tip of the optical fiber 15. The treatment may be made by cutting or welding. In this modification, the light irradiation portion 16 is configured by an extremely simple method, in which the shape of the optical fiber 15 itself is modified or machined to form, for example, the bent portion 16m and the collimator-lens treatment 16n, without using other members. In this modification, the light irradiation portion 16 is fixed to the tip end side 12c of the wire member 12 so that the shape of the bent portion 16m is not deformed.

In the first embodiment, a pipe-like (hollow) member may be used for the tip end side 12c of the wire member 12 so that the optical fiber 15 is passed through the hollow portion. Alternatively, the cap 16a may be extended so that it serves as the tip end side 12c of the wire member 12.

Embodiment 2

Figure 7:
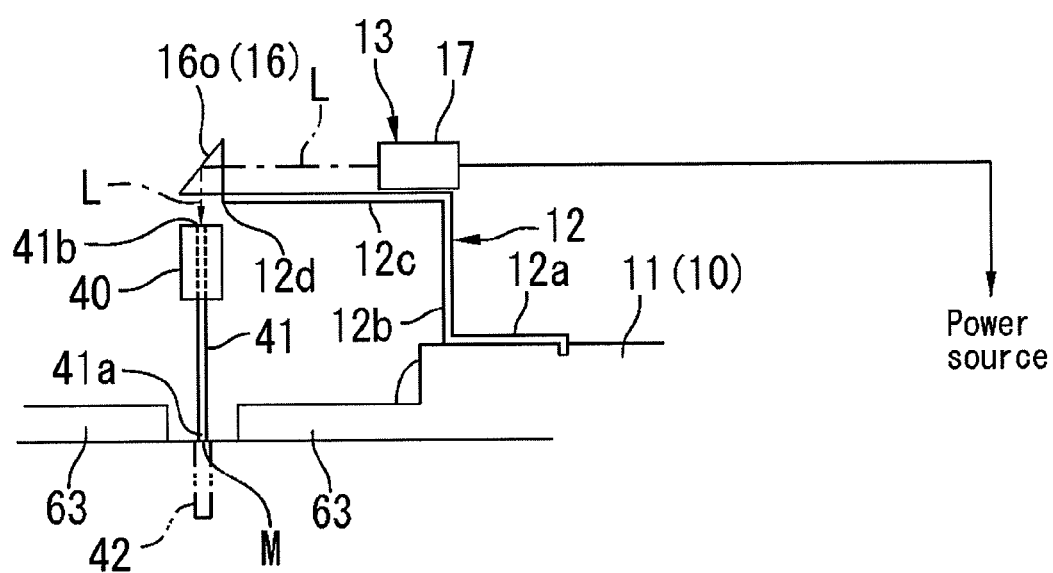
FIG. 7 is a schematic view illustrating a light irradiation apparatus 13 in a second embodiment.
Figure 8:
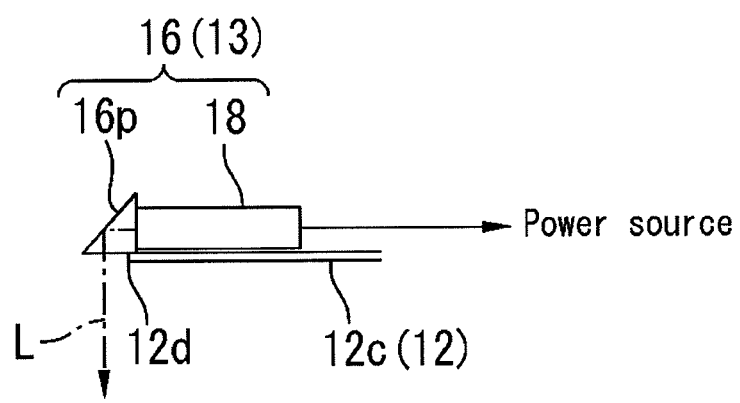
FIG. 8 is a schematic view illustrating a modification of the light irradiation portion 16 in the second embodiment.

The surgical guide 10 of a second embodiment is described with reference to FIG. 7 and FIG. 8. FIG. 7 is a schematic view illustrating the light irradiation apparatus 13 of the second embodiment. FIG. 8 is a schematic view illustrating a modification of the light irradiation portion 16 of the second embodiment.

The second embodiment is similar to the first embodiment in that a laser pointer (laser module with a collimator lens) 17 as a light emitting portion and a prism 16o as the light irradiation portion 16 are discretely formed. However, these portions are not coupled with an optical fiber, in the second embodiment. The laser light beam L emitted from the laser pointer 17 passes through open space, and reaches the prism 16o. The cylindrical laser pointer 17 is fixed near the intermediate portion 12b of the tip end side 12c of the wire member 12 as shown in FIG. 7. The prism 16o is fixed near the tip end 12d of the tip end side 12c. In the second embodiment, if the relative positioning between the laser pointer 17 and the prism 16o is deviated, the laser light beam L emitted from the laser pointer 17 does not impinge on the prism 16o. Therefore, the tip end side 12c of the wire member 12 is made non-deformable such that the relative positioning between the laser pointer 17 and the prism 16o is maintained, and the laser light beam L emitted from the laser pointer 17 impinges on the prism 16o and irradiates downward from the prism 16o. As a result, in the second embodiment, the relative positioning between the laser pointer 17 and the prism 16o is maintained without deforming the tip end side 12c of the wire 12 even in a case where the prism 16o is moved to make fine adjustments of the position or angle thereof. In the second embodiment, the angle or orientation of the inclination of the intermediate portion 12b of the wire member 12 may be mainly changed if the position of the prism 16o is moved.

The second embodiment has a very simple configuration in which only the prism 16o is mounted to the light irradiation portion 16 near the tip end 12d of the wire member 12.

A modification in the second embodiment is described with reference to FIG. 8. In this modification, the mounting position of the laser pointer 17 shown in FIG. 7 is moved to the tip end 12d of the tip end side 12c of the wire member 12, adjacently to the prism 16o.

In the modification, the light irradiation portion 16 is configured by a thin laser pointer 18 as a light emitting portion and a prism 16p being mounted to a tip of the laser pointer 18, as shown in FIG. 8. The light irradiation portion 16 serves as the light irradiation apparatus 13.

In the second embodiment, a reflection mirror may be used instead of the prism 16p (or 16o).

Embodiment 3

Figure 9:
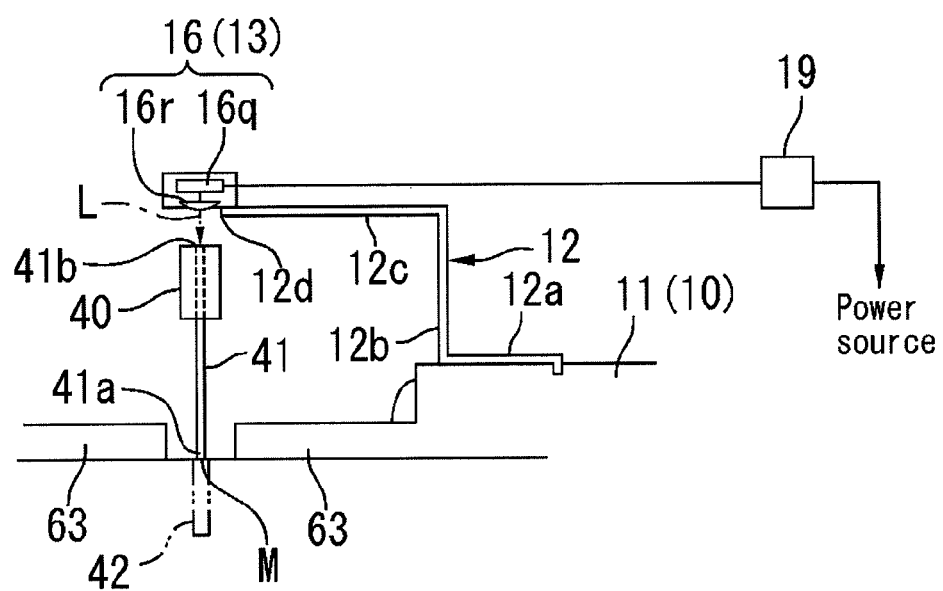
FIG. 9 is a schematic view illustrating the light irradiation apparatus 13 in a third embodiment.

The surgical guide 10 of a third embodiment is illustrated with reference to FIG. 9. FIG. 9 is a schematic view illustrating the light irradiation apparatus 13 in the third embodiment. The light irradiation portion 16 in the third embodiment is configured by a super-small laser diode 16q and a collimator lens 16r that are integrally formed. The light irradiation portion 16 itself serves as the entire light irradiation apparatus 13. The light irradiation portion 16 is mounted to the tip end 12d of the wire member 12. The laser light beam L emitted from the laser diode 16q passes through the collimator lens 16r disposed below the laser diode 16q, and irradiates toward the wire 31 (see FIG. 1). In the third embodiment, the laser diode 16q may be coupled to a power source, for example, via a current controlled APC (automatic power controller) 19 in order to control the light amount of the laser light beam L emitted from the laser diode 16q as appropriate.

In the third embodiment, a laser pointer (with built-in collimator lens and APC) may be used instead of the laser diode 16q. However, in that case, the degree the patient needs to open the mouth may become larger depending on the thickness of the laser pointer, and the use at a premolar tooth portion may become difficult.

In any of these embodiments, the diameter of the laser light beam L can be limited by mounting a dot aperture at the tip thereof. The dot aperture may be a structure other than the structure described above, and may be created by forming a hole having a diameter of about 0.1 mm in a thin metal plate or plastic plate, or by depositing a metal directly onto a collimator lens or a prism.

Embodiment 4

Figure 12A:
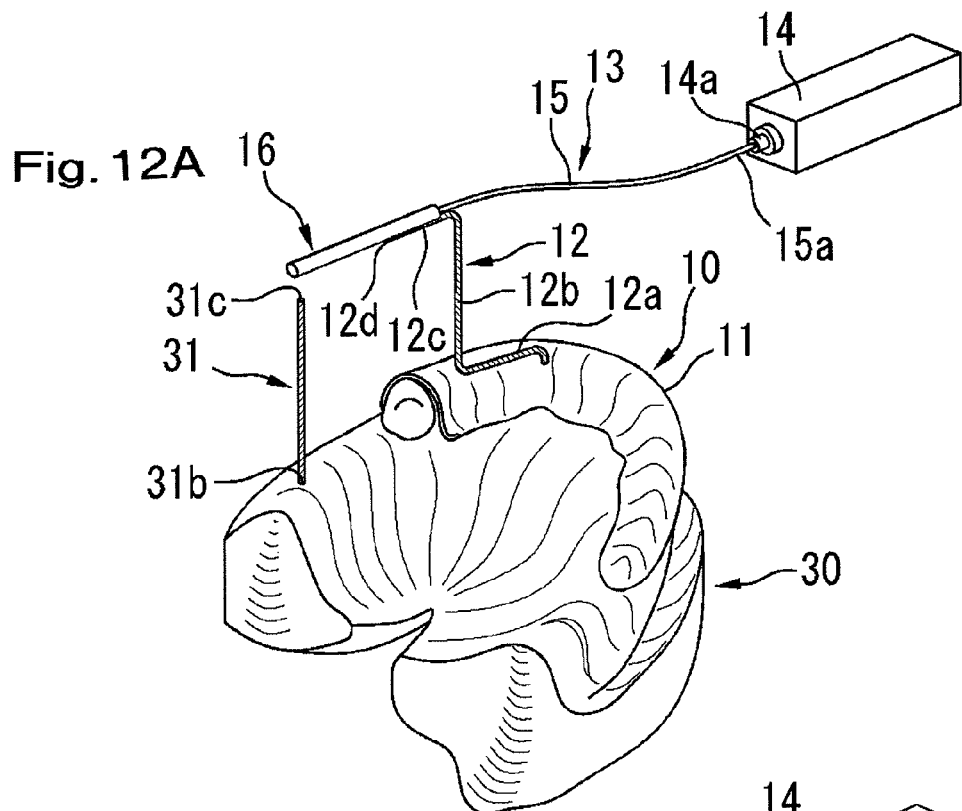
FIGS. 12A and 12B illustrate the surgical guide 10 in a fourth embodiment.
Figure 12B:
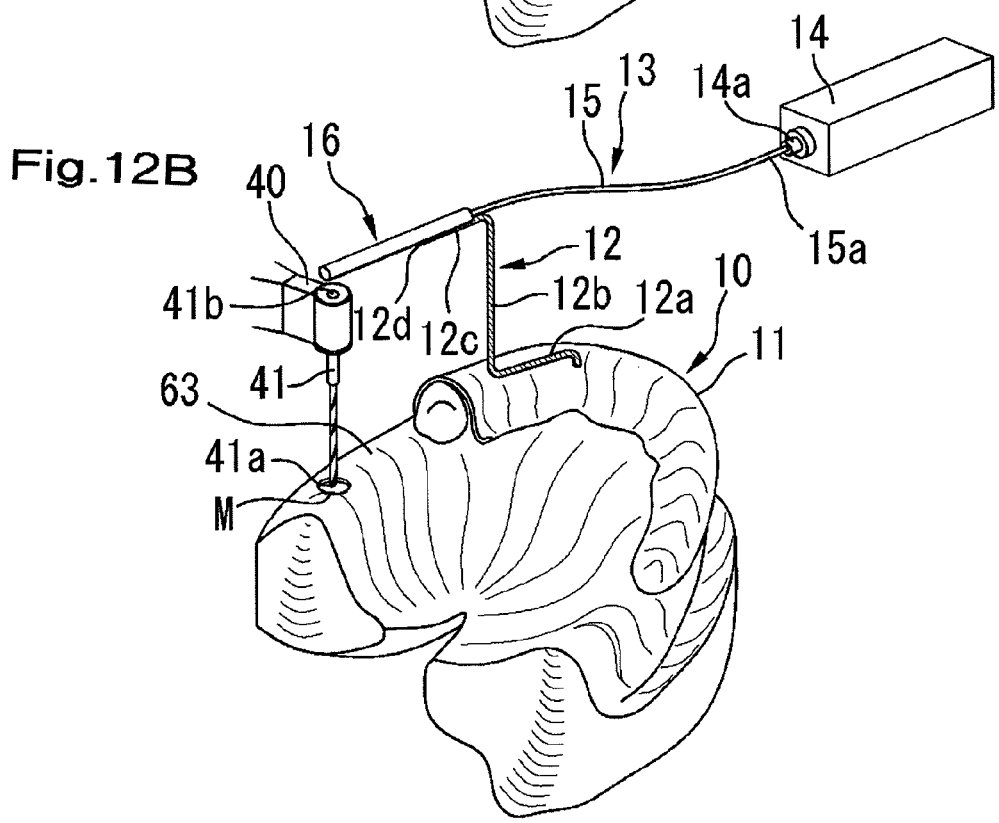
Figure 13:
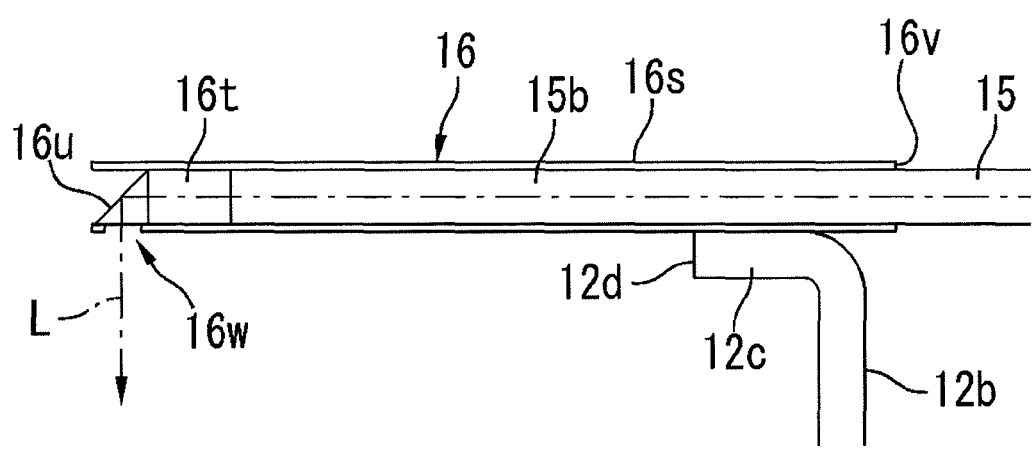
FIG. 13 is a schematic view (cross sectional view) illustrating the light irradiation portion 16 of the light irradiation apparatus 13 in the fourth embodiment.

The surgical guide 10 in a fourth embodiment is described with reference to FIGS. 12A, 12B and FIG. 13. FIG. 12A is a perspective view illustrating a condition in which the surgical guide 10 is mounted to the mockup 30. FIG. 12B is a perspective view illustrating the surgical guide 10 mounted in the mouth of a patient. FIG. 13 is a schematic view (cross sectional view) illustrating the light irradiation portion 16 of the light irradiation apparatus 13 in the fourth embodiment.

The light irradiation portion 16 of the light irradiation apparatus 13 in the fourth embodiment includes a pipe 16s that covers a tip portion 15b of the optical fiber 15, a collimator lens 16t disposed at a tip of the tip portion 15b of the optical fiber 15, and a prism 16u disposed at a tip of the collimator lens 16t, as shown in FIG. 13. The pipe 16s has a hollow pipe-like shape having the inner diameter of about 0.5 mm to 1 mm, for example, and has an opening 16v, into which the tip portion 15b of the optical fiber 15 is inserted, on the base end side (right side in FIG. 13). In addition, a circular window portion 16w is formed at a tip portion of the pipe 16s at the position that corresponds to a level surface (lower surface) of the prism 16u. In the fourth embodiment, a super-small cylindrical GRIN lens having the outer diameter of 0.5 mm to 1 mm is adopted as the collimator lens 16t. The laser light beam L guided in the optical fiber 15 from the base end portion 15a to the tip portion 15b becomes a beam-like light beam L when it passes through the collimator lens 16t. The light beam L is totally reflected on the inclined surface of the prism 16u, at which the orientation of the laser light beam L is changed downward at 90 degrees. The laser light beam L is emitted from the window portion 16w of the pipe 16s. The light irradiation portion 16 is mounted (fixed) to the tip end side 12c of the wire member 12 such that the base end side of the pipe 16s is disposed near the intermediate portion 12b of the wire member 12, as shown in FIG. 13. The length of the tip end side 12c of the wire member 12 is set to a length that is enough for retaining the position and angle of the pipe 16s.

According to the fourth embodiment, the cylindrical GRIN lens having a super-small outer diameter is adopted. Therefore, the pipe 16s can be made extremely narrow, and the tip end side 12c of the wire member 12 can be shortened. As a result, the size of the portion of the surgical guide 10 that is inserted into a back portion of the mouth of the patient can be made extremely small, and the surgical guide 10 is suitable especially for the implant treatment for a molar teeth portion.

Embodiment 5

Figure 14A:
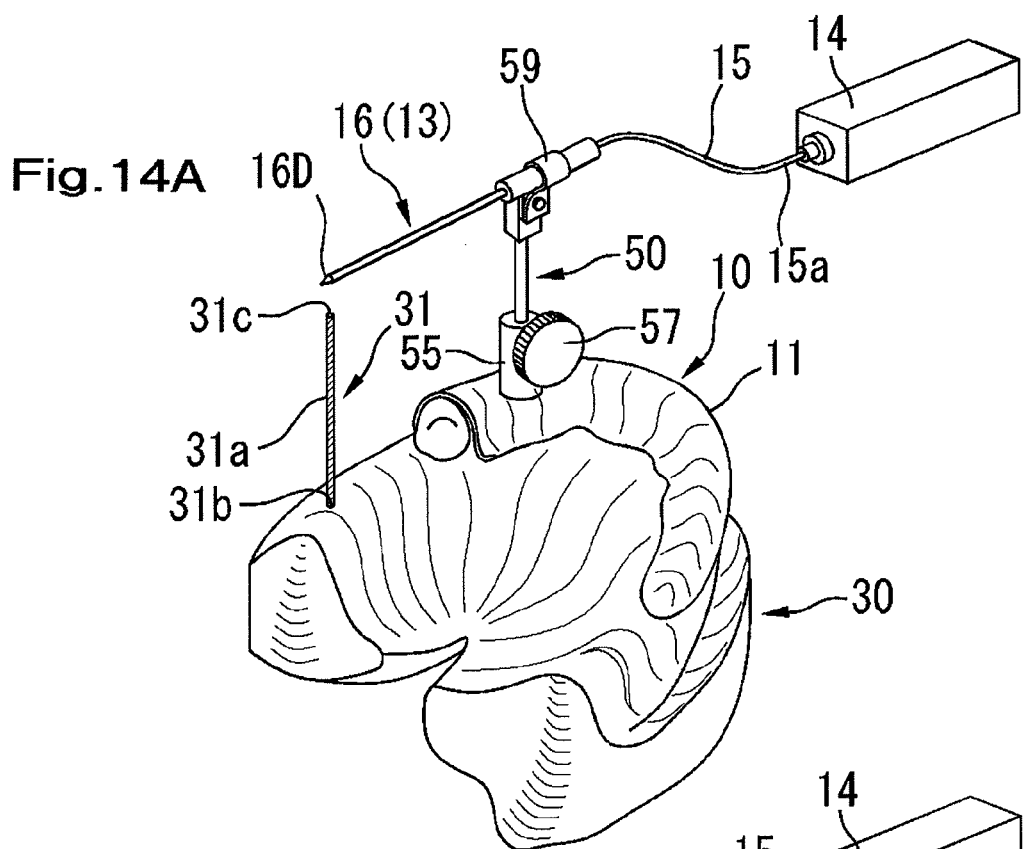
FIGS. 14A and 14B are perspective views illustrating the surgical guide 10 in a fifth embodiment.
Figure 14B:
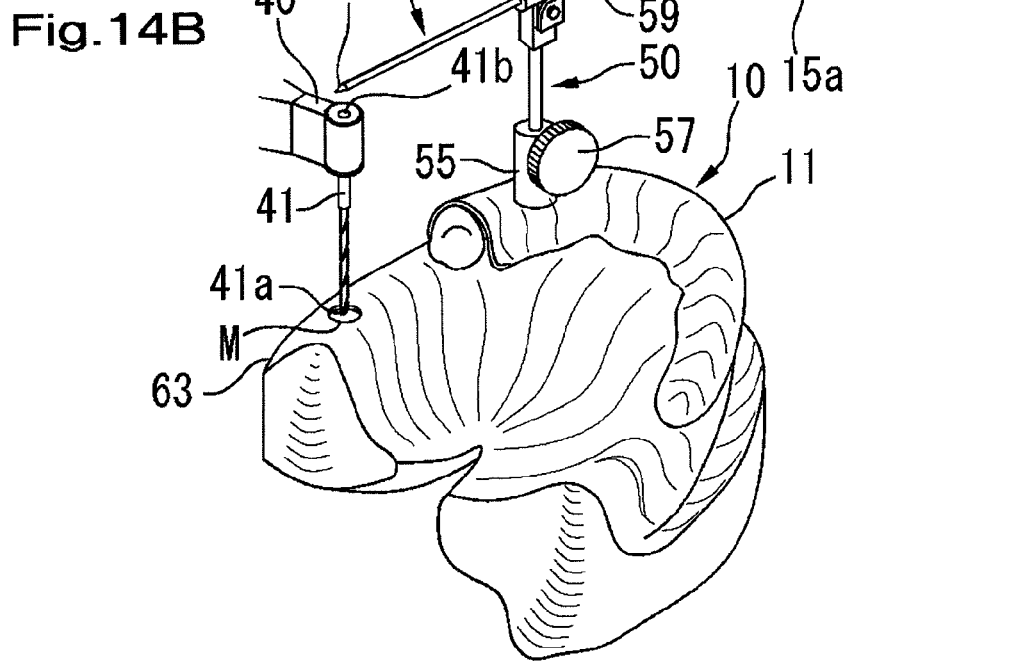
Figure 16A:
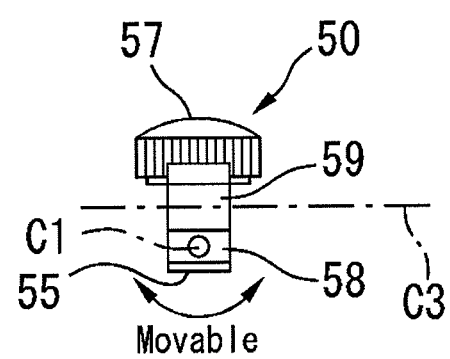
FIGS. 16A to 16C are three views of a supporting member 50.
Figure 16B:
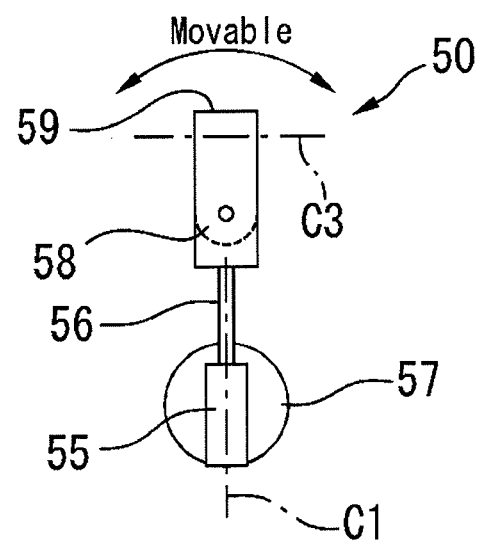
Figure 16C:
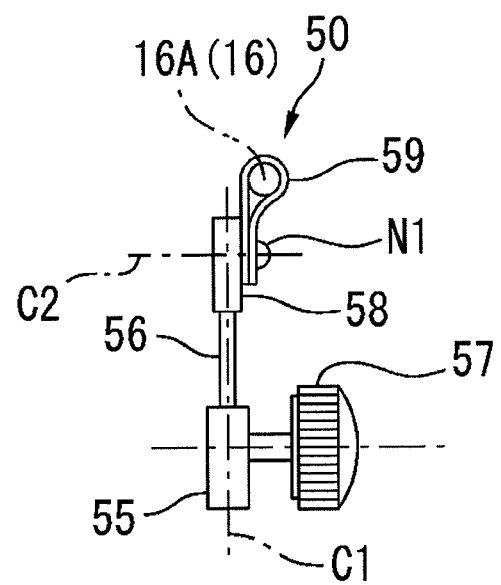

The surgical guide 10 in a fifth embodiment is described with reference to FIGS. 14A and 14B, FIGS. 15A and 15B, and FIGS. 16A to 16C. FIG. 14A is a perspective view illustrating a condition in which the surgical guide 10 is mounted to the mockup 30. FIG. 14B is a perspective view illustrating the surgical guide 10 mounted in the mouth of a patient. FIG. 15A is a schematic view (cross sectional view) illustrating the light irradiation portion 16 of the light irradiation apparatus 13 of the fifth embodiment. FIG. 15B is a schematic view (cross sectional view) illustrating a modification of the light irradiation portion 16. FIGS. 16A to 16C are three views of a supporting member 50 that is a supporting member different from the wire member 12. FIG. 16A is a top view, and FIG. 16B is a side view, and FIG. 16C is a front view.

In the fifth embodiment, the supporting member 50 is used for a supporting member, instead of the wire member 12. As shown in FIGS. 16A to 16C, the supporting member 50 includes a cylindrical shaft holder 55, which is mounted to the guide member 11, shown at the lower end of FIG. 16C. A shaft 56 is inserted into the shaft holder 55 from above. The shaft 56 has a lower end being fixed to the shaft holder 55 with a knurled screw 57. A block-shaped base member 58 is mounted to an upper end of the shaft 56. A female screw is threaded into the base member 58 laterally in FIG. 16C. A male screw N1 is screwed to the female screw to fix a holder 59 to the base member 58. The holder 59 is a member used for retaining the light irradiation portion 16 (cover 16A) of the light irradiation apparatus 13 described later, and is formed by folding or bending a strip of a metal plate. More specifically, the holder 59 is formed such that a vertical portion fixed with the male screw N1 is bent circularly along the outer periphery of the light irradiation portion 16 (cover 16A), and extended downward and fixed again with the male screw N1, in FIG. 16C.

The supporting member 50 having a configuration as described above is capable of moving and adjusting the light irradiation portion 16 at a given position and a given angle. In other words, the height can be adjusted by loosing the knurled screw 57 and moving the shaft 56 up or down. In addition, the rotational direction around the center axis C1 can be adjusted by loosing the knurled screw 57 and rotating the shaft 56 around the center axis C1. In addition, the rotational direction around the center axis C2, i.e. the swinging up or down, can be adjusted by loosing the male screw N1. In addition, the holder 59 can be moved to the direction of the center axis C3 by loosing the male screw N1. Moreover, the rotational direction around the center axis C3 can be adjusted by loosing the male screw N1.

As described above, the supporting member 50 is capable of moving and adjusting the light irradiation portion 16 at given position and angle, and concurrently capable of fixing the light irradiation portion 16 to retain the position and angle, by combining the movement and adjustment as described above as appropriate.

The light irradiation portion 16 of the light irradiation apparatus 13 in the fifth embodiment includes a cover 16A covering the tip portion 15b of the optical fiber 15, a collimator lens 16B disposed at a tip of the tip portion 15b of the optical fiber 15, a pipe 16C mounted to a tip of the cover 16A, and a prism 16D mounted to a tip of the pipe 16C as shown in FIG. 15A. The cover 16A has a hollow pipe-like shape having the inner diameter of about 3 mm to 4 mm, and is retained by the holder 59 of the supporting member 50 described above. The pipe 16C has a hollow pipe-like shape having the inner diameter of about 0.5 mm to 1 mm. The pipe 16C has a circular window portion 16E formed at a tip portion of the pipe 16C, at the position that corresponds to a level surface (lower surface) of the prism 16D. The laser light beam L guided in the optical fiber 15 from the base end portion 15a to the tip portion 15b becomes a beam-like light beam L when it passes through the collimator lens 16B. The light beam L goes though the pipe 16C, and impinges on the vertical plane (side surface) of the prism 16D. The light beam L is totally reflected on the inclined surface of the prism 16D, at which the orientation of the light beam L is changed downward at 90 degrees. The light beam L is emitted from the window portion 16E of the pipe 16C.

The light irradiation portion 16 in the fifth embodiment achieves a size as small as the light irradiation portion 16 of the fourth embodiment, without using an expensive GRIN lens. However, the beam-like light beam L that passes through the collimator lens 16B will not impinge on the vertical plane (side surface) of the prism 16D if the pipe 16C is deformed even slightly. Therefore, no stress should be applied on the pipe 16C when the position and angle of the light irradiation portion 16 is moved and adjusted in the fifth embodiment. As a result, a supporting member such as the supporting member 50 is essentially required.

FIG. 15B illustrates a modification of the light irradiation portion 16 in the fifth embodiment. The optical fiber 15 in the light irradiation portion 16 shown in FIG. 15A described above is replaced with a small laser diode (or laser module) 14b (light emitting portion) in the light irradiation portion 16 of this modification. The small laser diode 14b is coupled to a power source via an APC (automatic power controller) 14c. Other configuration is similar to that of the light irradiation portion 16 described above. In this modification, the light irradiation portion 16 itself serves as the light irradiation apparatus 13.

In any of the embodiments described above, a reflection mirror may be used instead of the prism.

In addition, in any of these embodiments, the beam diameter of the laser light beam L can be limited by mounting a dot aperture at the tip thereof. The dot aperture may be a structure other than the structure in the first embodiment described above, and may be created by forming a hole having a diameter of about 0.1 mm in a thin metal plate or plastic plate, or by depositing a metal directly on a collimator lens or a prism. However, interference fringes may occur due to diffraction of the light, depending on the wavelength of the light or the diameter of the dot aperture. In that case, the profile of bright points (beam spots) of the light will become clearer when the dot aperture is not mounted.

Furthermore, the position the light irradiation portion 16 is to be mounted relative to the guide member 11 can made be lower, if a drill having a shorter length is used for the drill 41. This may reduce the burden of the patient, who otherwise needs to widely open the mouth during the treatment. Therefore, this approach is convenient especially for the implant treatment for a molar teeth portion.

In addition, a DPSS laser (diode pumped solid state laser) may be used for a semiconductor laser that is used as the laser light source 14, other than the laser diode described above. The wavelength of the laser beam can be selected in a range from 405 nm to 780 nm. An adequate output may be in a range from about 1 mW to 10 mW.

An optical fiber of any of a multi mode, a single mode, or a PM mode (polarization maintaining mode) having the outer diameter of about 0.5 mm to 1.5 mm may be used for the optical fiber 15. An optical fiber of a single mode fiber, which can make the outer diameter of the beam spots (bright points) smaller, is more preferable to a multi mode optical fiber. Also, a coupler 14a (see FIGS. 12A and 12B) is required for coupling (connecting) the laser light source 14 and the optical fiber 15.

In addition, a polycarbonate sheet, which can be shaped such that it conforms to the mockup 30 by vacuum press (not shown), may be used for a material of the guide member 11 of the surgical guide 10, the guide member 21 of the surgical guide 20, and the wire guide 22, other than the resin described above. An adequate thickness for the sheet in those cases may be in a range from 1.5 mm to 2 mm.

Furthermore, the stiffness of the wire member 12 as a supporting member can be increased by using a wire that is thicker than the wire 31 and 32 for the wire member 12. This may reduce the risk that the wire member 12 is inadvertently deformed. However, in this case, a tool such as a plier is required to plastically deform the wire member 12.

Advantages according to the first to fifth embodiments described above include:

(1) A dentist can observe the surgical site. The dentist does not feel uneasy because the dentist can perform drilling operation while visually identifying the portion of the alveolar bone the tip of the drill 41 is cutting.

(2) It can be prevented that the drill 41 tilts more than necessary, by performing drilling operation while the orientation of the contra head 40 is adjusted such that the light beam L continues to irradiate the center of the base end portion 41b of the drill 41 without deviating therefrom.

(3) Sufficient cooling water can be supplied to the portion at which the hole is formed, which is less likely to cause bone burns.

(4) Various drills 41 having different diameters are generally used in order to form a guide hole into which the fixture 71 is to be embedded. At first, a drill (pilot drill) 41 having a small diameter is used, and then drills 41, each having a slightly larger diameter than the diameter of the drill used in the preceding drilling, are used. Nevertheless, a same surgical guide can be used for the drills 41 each having a different diameter. This saves cost for additional surgical guides otherwise required.

(5) The present embodiments can be applied to either of a flapping approach in which the mucosa is stripped so that the bone surface is widely exposed, or a flapless approach in which a hole, which is large enough to insert the fixture therein, is punched in the mucosa.

(6) In conventional technology, the guide ring contacts the drill, and thus the vibration of the drill causes the guide member to be easily detached or become unstable; however, the present embodiments are free from such disadvantages.

(7) A dentist can imagine (simulate) the operation in a condition substantially same as that of an actual operation through a practice, in which the dentist mounts the surgical guide 10 to the mockup 30 from which the wire 31 and the wire 32 are removed, and adjusts the orientation of the contra head 40 such that the central axis of the drill 41 is aligned with the optical axis of the light beam L on the mockup 30.

10, 20: surgical guide
11, 21: guide member
12: wire member (supporting member)
12a: base end side (base end portion)
12b: intermediate portion
12c: tip end side (tip end portion)
12d: tip end
13: light irradiation apparatus
14: laser light source (laser module as a light emitting portion)
14a: coupler
14b: small laser diode (or laser module)
14c: APC
15: optical fiber
15a: base end portion of an optical fiber
15b: tip portion of an optical fiber
16: light irradiation portion
16a: cap
16b: inclined Surface
16c, 16k, 16n, 16r, 16B: collimator lens
16d: dot aperture
16e: opening of a cap
16f: lid of a cap
16g: window portion of a cap
16h: glass plate
16i: surface of a glass plate
16j, 16o, 16p, 16u, 16D: prism
16m: bent portion
16q: super-small laser diode
16s, 16C: pipe
16t: collimator lens (GRIN lens)
16v: opening of a pipe
16w, 16E: window portion of a pipe
17: laser pointer
18: thin laser pointer
19: current-controlled APC
30: mockup (plaster model)
31, 32: wire
31a, 32a: protruding portion of a wire
31b, 32b: base end portion of a wire
31c, 32c: tip portion of a wire
40: contra head
41: drill (pilot drill)
41a: tip of a drill
41b: base end portion of a drill
42: embedding hole (guide hole)
50: supporting member
63: mucosa
70: implant (dental implant)
71: fixture
L: light, laser light, light beam
M: mark
R: the radius of curvature

The invention claimed is:

1. A method for positioning a drill
using a surgical guide for reproducing in the mouth of a patient the position and orientation of the drill with respect to a wire embedded in a mockup that imitates inside of the mouth of a patient with for indicating the position and orientation of the drill when a guide hole into which a dental implant fixture is embedded is formed, the surgical guide comprising:
a detachably attachable guide member to be fitted to a tooth portion of the mockup and to a tooth portion of the patient that corresponds to the tooth portion of the mockup,
a light irradiation apparatus that comprises a light emitting portion for emitting light, and a light irradiation portion for irradiating the light emitted at the light emitting portion as a spot-beam like light beam toward a tip of the wire, and
a supporting member having a the base end portion mounted to the guide member, and further having a tip end portion capable of supporting at least the light irradiation portion of the light irradiation apparatus such that the irradiating position and irradiating angle of the light beam that is irradiated from the light irradiation portion toward the tip of the wire can be adjusted, the method comprising:
fitting the guide member to the tooth portion of the mockup, and moving and adjusting the light irradiation portion supported by the supporting member such that the spot-beam like light beam is aligned with the central
removing the guide member from the tooth portion of the mockup, and fitting the guide member to the tooth portion of the patient such that the central axis of the drill is aligned with the spot-beam like light beam.

* * * * *

UNITED STATES PATENT AND TRADEMARK OFFICE
CERTIFICATE OF CORRECTION

PATENT NO. : 8,678,819 B2  Page 1 of 1
APPLICATION NO. : 12/992670
DATED : March 25, 2014
INVENTOR(S) : A. Takebayashi It is certified that error appears in the above-identified patent and that said Letters Patent is hereby corrected as shown below:

In the Claims

Column 16, line 20 (claim 1, line 5), please change "patient with for indicating"
to -- patient for indicating --

Column 16, line 33 (claim 1, line 33), please change "a the base" to -- a base --

Column 16, line 44 (claim 1, line 29, 30), please change "central removing" to
-- central axis of the wire; and removing --

Signed and Sealed this
Fifth Day of August, 2014

Michelle K. Lee
*Deputy Director of the United States Patent and Trademark Office*